US011026894B2

(12) United States Patent
Irvine et al.

(10) Patent No.: US 11,026,894 B2
(45) Date of Patent: Jun. 8, 2021

(54) LIPID NANOPARTICLES AND USE THEREOF TO DELIVER RNA POLYNUCLEOTIDES

(71) Applicant: Massachusetts Institute of Technology, Cambridge, MA (US)

(72) Inventors: Darrell J. Irvine, Arlington, MA (US); Ron Weiss, Newton, MA (US); Tasuku Kitada, Cambridge, MA (US); Mariane Melo, Stoneham, MA (US); Yuan Zhang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/739,197

(22) Filed: Jan. 10, 2020

(65) Prior Publication Data
US 2020/0222332 A1    Jul. 16, 2020

Related U.S. Application Data

(60) Provisional application No. 62/954,062, filed on Dec. 27, 2019, provisional application No. 62/790,589, filed on Jan. 10, 2019.

(51) Int. Cl.
A61K 9/51    (2006.01)
A61P 35/00   (2006.01)
A61K 9/00    (2006.01)
A61K 38/20   (2006.01)

(52) U.S. Cl.
CPC .......... *A61K 9/5123* (2013.01); *A61K 9/0019* (2013.01); *A61K 38/2086* (2013.01); *A61P 35/00* (2018.01)

(58) Field of Classification Search
CPC .............. A61K 9/5123; A61K 38/2086; A61K 9/0019; A61K 9/1272; A61K 48/003; A61P 35/00
See application file for complete search history.

(56) References Cited

FOREIGN PATENT DOCUMENTS

| WO | WO 2013/006825 A1 | 1/2013 |
| WO | WO 2016/131052 A1 | 8/2016 |
| WO | 2017201350 A1 * | 11/2017 |
| WO | WO 2017/201350 A1 | 11/2017 |
| WO | WO 2019/023566 A1 | 1/2019 |

OTHER PUBLICATIONS

Li et al, Nanoscale Platforms for Messenger RNA Delivery, Wiley Interdiscip Rev Nanomed Nanobiotechnol. Mar. 2019; 11(2): e1530. (Year: 2019).*

(Continued)

*Primary Examiner* — Carlos A Azpuru
(74) *Attorney, Agent, or Firm* — Wolf, Greenfield & Sacks, P.C.

(57) ABSTRACT

Disclosed herein are lipid nanoparticles comprising 1,2-dioleoyl-3-trimethylammonium propane (DOTAP), 1,2-distearoyl-sn-glycero-3-phosphocholine (DSPC), cholesterol, and 1,2-distearoyl-sn-glycero-3-phosphoethanolamine-N-[amino(polyethylene glycol)-2000](DSPE-PEG2000), compositions including such lipid nanoparticles, and methods of treatment using such lipid nanoparticles and compositions.

21 Claims, 18 Drawing Sheets

(56) References Cited

OTHER PUBLICATIONS

Hosseini et al,Cholesterol-rich lipid-mediated nanoparticles boost of transfection efficiency, utilized for gene editing by CRISPR-Cas9, International Journal of Nanomedicine, Journal 14, pp. 4353-4366. (Year: 2019).*

International Search Report and Written Opinion dated Apr. 17, 2020 for Application No. PCT/US2020/013024.

Stone et al., Design and characterization of a protein superagonist of IL-15 fused with IL-15Ralpha and a high-affinity T cell receptor. Biotechnol Prog. Nov.-Dec. 2012;28(6):1588-97. doi: 10.1002/btpr.1631. Epub Oct. 18, 2012.

* cited by examiner

LIPID NANOPARTICLES AND USE THEREOF TO DELIVER RNA POLYNUCLEOTIDES

CROSS-REFERENCE TO RELATED APPLICATIONS

This application claims priority under 35 U.S.C. § 119(e) to U.S. Provisional Application No. 62/790,589, filed on Jan. 10, 2019, and U.S. Provisional Application No. 62/954,062, filed on Dec. 27, 2019, the entire contents of each of which is incorporated by reference herein in its entirety.

GOVERNMENT SUPPORT

This invention was made with Government support under Grant No. W911NF-11-2-0054 awarded by the Army Research Office. The Government has certain rights in the invention.

FIELD

Disclosed herein are lipid nanoparticles having a specific composition, compositions including such lipid nanoparticles, and methods of treatment using such lipid nanoparticles and compositions.

BACKGROUND

Strategies to introduce genes to tumors amenable to systemic delivery have been extensively studied, including DNA formulated in nanoparticles or recombinant viral vectors, but these methods suffer from the low efficiency of DNA delivery by synthetic materials and issues of anti-vector immunity, respectively. Delivery of mRNA by synthetic formulations is also a possibility, but delivery of mRNA leads to very short expression times of typically only a few days in vivo. Clearly, there is a need in the art for new compositions and methods for delivering genes to tumors with a higher efficiency of delivery and/or a longer expression time. The present disclosure addresses this need.

SUMMARY

Described herein are lipid/polymer nanoformulations with alphavirus replicon RNA, which are capable of transducing solid tumors in vivo following intratumoral or systemic delivery, and which can express a therapeutic gene circuit that has substantial anti-tumor activity. These formulations form the basis for delivery of a variety of potential genetic circuits from one or more replicon RNAs. Two alternative formulations for replicon delivery, LNPs (lipid nanoparticles) and LPRs (lipid-protamine nanoparticles) are described herein.

According to one aspect, the disclosure provides lipid nanoparticles (LNPs) comprising or consisting of 1,2-dioleoyl-3-trimethylammonium propane (DOTAP), 1,2-distearoyl-sn-glycero-3-phosphocholine (DSPC), cholesterol, and 1,2-distearoyl-sn-glycero-3-phosphoethanolamine-N-[amino(polyethylene glycol)-2000] (DSPE-PEG2000), wherein the molar ratio of DOTAP:DSPC:cholesterol:DSPE-PEG2000 is about 40:about 10:about 48:about 2. In some embodiments, the LNPs. In some embodiments, the LNPs comprise or consist of 1,2-dioleoyl-3-trimethylammonium propane (DOTAP), 1,2-distearoyl-sn-glycero-3-phosphocholine (DSPC), cholesterol, and 1,2-distearoyl-sn-glycero-3-phosphoethanolamine-N-[amino(polyethylene glycol)-2000] (DSPE-PEG2000), wherein the molar ratio of DOTAP:DSPC:cholesterol:DSPE-PEG2000 is 40:10:48:2. In some embodiments, the lipid nanoparticle is about 100 nM in diameter. In certain embodiments, the surface charge of the lipid nanoparticle is about neutral, or it is about neutral to about 25 mV.

According to another aspect, compositions are provided that include the described lipid nanoparticles and an alphavirus replicon.

In some embodiments, the compositions include a pharmaceutically acceptable carrier. In some embodiments, the alphavirus replicon includes a gene encoding a therapeutic agent. In some embodiments, the therapeutic agent is a cytokine, a chemokine, or a growth factor.

In some embodiments, the disclosure provides a composition comprising an LNP disclosed herein and one or more RNA polynucleotide. In some embodiments, the one or more RNA polynucleotide comprises one or more self-replicating RNA derived from an alphavirus. In certain embodiments, the alphavirus is a Venezuelan equine encephalitis virus, e.g., Venezuelan equine encephalitis virus TC-83 or a variant thereof. In particular embodiments, at least one of the self-replicating RNA comprises a 5' cap. In certain embodiments, the ratio of cationic amines in the lipid nanoparticle to anionic phosphates in the self-replicating RNA (N:P ratio) is about 0.5:1 to about 20:1. In some embodiments, at least one of the self-replicating RNA comprises a sequence encoding a therapeutic agent. In some embodiments, it encodes a cytokine, a chemokine, or a growth factor. In some embodiments, the therapeutic agent is an anti-tumor agent, e.g., interleukin-15 (IL-15) or an IL-15 superagonist. In some embodiments, the composition comprises two or more self-replicating RNAs, optionally wherein the self-replicating RNA is present within the lipid nanoparticle.

According to another aspect, methods of treatment are provided. The methods include administering to a subject in need of such treatment the lipid nanoparticles or compositions described herein. In some embodiments, the subject has cancer. Thus, the disclosure provides a method of treating a disease or disorder in a subject in need thereof, comprising providing to the subject a composition disclosed herein, wherein the RNA polynucleotide, e.g., self-replicating RNA, comprises a sequence encoding a therapeutic agent, e.g., polypeptide. In some embodiments, the disease or disorder is a cancer, and the therapeutic agent is an anti-tumor agent. In some embodiments, the cancer is a skin cancer, optionally a melanoma, a breast cancer, a head and neck cancer, or a lymphoma. In some embodiments, the anti-tumor agent is interleukin-15 (IL-15) or an IL-15 superagonist. In certain embodiments, the composition is provided to the subject systemically or locally, optionally intratumorally. In certain embodiments, the composition is provided to the subject parenterally, optionally intravenously. In some embodiments, the composition is provided in one or more doses. In some embodiments, the composition is provided in two or more doses within two weeks of each other. In some embodiments, the composition is provided at about 1 µg/dose to about 1000 µg/dose. In some embodiments, the treatment inhibits tumor growth by at least 10% as compared to growth of an untreated tumor. In some embodiments, the treatment results is reduced tumor volume of at least 10% as compared to the size of an untreated tumor.

The subject matter of this application may involve, in some cases, interrelated products, alternative solutions to a particular problem, and/or a plurality of different uses of a single system or article. These and other aspects of this disclosure, as well as various embodiments thereof, will become more apparent in reference to the drawings and detailed description. Additionally, the subject matter disclosed herein is not limited in its application to the details of construction and the arrangement of components set forth in the following description or illustrated in the drawings. It is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. For purposes of clarity, not every component may be labeled in every drawing. It is to be understood that the data illustrated in the drawings in no way limit the scope of the disclosure. In the drawings:

(FIG. 1A) Tumor growth inhibition. (FIG. 1B) Relative body weight changes (normalized to day 0). (FIG. 1C) Tumor weights at the end point of the therapy on day 16. Tumor lysates were collected at the end of therapy, and the (FIG. 1D) IL15 and (FIG. 1E) IFNγ levels were measured by ELISA.

(FIG. 2A) Tumor growth inhibition. (FIG. 2B) Relative body weight changes (normalized to day 0). (FIG. 2C) Survival curve. At 0 percent survival, the lines from left to right are as follows: control, soluble FLuc2, soluble IL15-Fc, LNP-FLuc2, and LNP-IL15-Fc.

(FIG. 4A) Tumor growth inhibition. (FIG. 4B) Relative body weight changes (normalized to day 0). (FIG. 4C) Survival curve. At 0 percent survival, the lines from left to right are as follows: PBS, LNP-FLuc2, free IL15-Fc, and LNP-IL15-Fc.

DETAILED DESCRIPTION

Figure 1A:
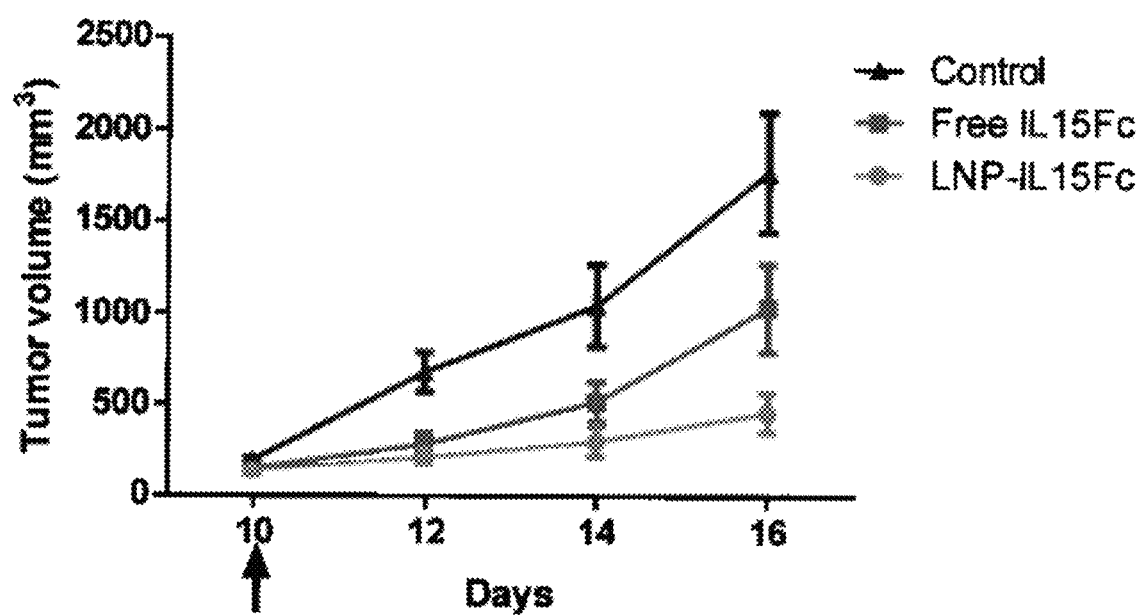
FIGS. 1A-1E. C57BL/6 mice were inoculated with 0.5M B16F10 cells subcutaneously in the right flank and given intratumoral injections on day 10, with 5 µg/dose.

The disclosure provides compositions and methods for delivering therapeutic gene products to cells, e.g., for the treatment of diseases or disorders. In particular embodiments, methods for delivering genetic programs to tumors enable the engineering of direct tumor cell death, tumor microenvironment remodeling, and or triggering of antitumor immune responses. In particular embodiments, the composition and methods disclosed herein are used to deliver self-replicating RNA derived from alphaviruses, which is shown to more efficiently transfects cells in vivo than DNA due to the lack of a requirement for nuclear delivery, and which is expressed much more persistently than mRNA due to its ability to self-copy within transfected cells.

Lipid Nanoparticles and Lipid-Protamine Nanoparticles

Described herein are lipid nanoparticles (LNPs) comprising 1,2-dioleoyl-3-trimethylammonium propane (DOTAP), 1,2-distearoyl-sn-glycero-3-phosphocholine (DSPC), cholesterol, and 1,2-distearoyl-sn-glycero-3-phosphoethanolamine-N-[amino(polyethylene glycol)-2000] (DSPE-PEG2000). In certain embodiments, these components of the LNP are present in the LNP at a molar ratio of about 40:about 10:about 48:about 2, respectively. In certain embodiments, the LNP comprises or consists of each of the following at a molar ratio in the ranges of: DOTAP (35-45): DSPC (8-12):cholesterol (40-60):DSPE-PEG2000 (0-4), inclusive of the recited values. In certain embodiments, the LNP comprises or consists of each of the following at a molar ratio in the ranges of: DOTAP (38-42):DSPC (9-11): cholesterol (43-53):DSPE-PEG2000 (1-3), inclusive of the recited values. LNPs having a 40:10:48:2 molar ratio of DOTAP:DSPC:cholesterol:DSPE-PEG2000 have been found to have unexpectedly superior effects for delivery of alphavirus replicons, as shown herein. In certain embodiments, the surface charge of the LNP is about neutral, or it is about neutral to about 25 mV.

As used herein, the term "about" indicates a range within 10% of an indicated value.

The LNPs can be produced by an ethanol dilution method described below (see Example 1), or other methods known to those skilled in the art.

The disclosure also provides lipid-protamine nanoparticles (LPRs) comprising DOTAP, cholesterol, and DSPE-PEG. In some embodiments, the LPRs comprise DOTAP and cholesterol at a molar ratio of about 1:about 1. In certain embodiments, the LPR comprises each of the following at a molar ratio in the ranges of: DOTAP (0.8-1.2):DSPE-PEG (0.8-1.2), inclusive of the recited values. In some embodiments, the molar ratio of the DOTAP:cholesterol is about 1:about 1. In some embodiments, the DOTAP:protamine molar ratio is about 16:about 1, or in the range of 40:1 to 5:1 or in range of 20:1 to 12:1. In particular embodiments, the LPR comprises an about 1% DSPE-PEG coating, or DSPE-PEG of about 0.2% to about 5%, or about 0.5% to about 2%. In certain embodiments, the surface charge of the LPR is about 25 mV, or it is about neutral to about 25 mV.

The LPRs can be produced as described below (see Example 2), or other methods known to those skilled in the art.

Compositions

Also provided herein are compositions comprising a lipid nanoparticle (LNP) disclosed herein, e.g., comprising a 40:10:48:2 molar ratio of DOTAP:DSPC:cholesterol:DSPE-PEG2000, and a RNA polynucleotide. In certain embodiments, the RNA polynucleotide is single-stranded, double-stranded, triple-stranded, or a combination thereof. In particular embodiments, the RNA polynucleotide comprises an expression cassette, which itself comprises a sequence encoding a polypeptide gene product operably linked to a promoter. In some embodiments, the RNA polynucleotide is a self-replicating RNA, e.g., an alphavirus replicon. In particular embodiments, the RNA polynucleotide is encapsulated within the LNP. In certain embodiments, the RNA polynucleotide is associated with the LNP, and in certain embodiments, the RNA polynucleotide is bound to the LNP. The compositions can further include a pharmaceutically acceptable carrier.

Also provided herein are compositions comprising an LPR disclosed herein, e.g., comprising DOTAP, cholesterol, DSPE-PEG, and a RNA polynucleotide, e.g., an alphavirus replicon. The compositions can further include a pharmaceutically acceptable carrier. In particular embodiments, the RNA polynucleotide is encapsulated within the LPR. In certain embodiments, the RNA polynucleotide is associated with the LPR, and in certain embodiments, the RNA polynucleotide is bound to the LPR.

In various embodiments of the composition and methods disclosed herein, the RNA polynucleotide is a self-replicating RNA derived from an alphavirus, including but not limited to any of the alphavirus disclosed herein.

A virus is a small pathogen that is only capable of replication inside a living host cell (e.g., prokaryotic and eukaryotic cells). Outside of living cells, viruses exist as independent particles (e.g., viral particles or virions), which comprise genetic material in the form of DNA or RNA, the latter of which can be single-stranded or double-stranded. Viruses with DNA are referred to as DNA viruses, and viruses with RNA are referred to as RNA viruses. In some cases, the virus comprises nucleic acid-associated proteins and the combination of the virus and nucleic acid-associated proteins is referred to as nucleoprotein. In addition to the genetic material, viruses have a single or double protein coat, also known as a capsid, which facilitates attachment of the virus to a living host cell's receptors during infection and protects the genetic material of the virus from enzymatic degradation. The combination of nucleoprotein and the capsid is referred to as a nucleocapsid. In some cases, viruses have a lipid bilayer envelope, studded with virus-coded, glycosylated (trans-) membrane-associated proteins. Once a virus has infected a living host cell, the virus is dependent on the living host cell to supply the machinery for its replication, and propagation thereafter. The viral genome codes for some structural proteins and non-structural regulatory proteins.

The term "structural protein," as used in the context of viruses herein, refers to proteins that constitute the structural components of mature assembled virus particles or virions. Non-limiting examples of such structural proteins include nucleocapsid core proteins (e.g., gag proteins), enzymes packaged within the virus particle (e.g., pol proteins), and membrane components (e.g., env proteins). In contrast, the term "non-structural protein," as used in the context of viruses herein, refer to proteins that are expressed within the host cell but do not constitute structural components of the virus particle or virion. Some of the roles of non-structural proteins include, but are not limited to, replicon formation, immunomodulation, and transactivation of structural protein genes.

As used herein, the term "replicon" refers to a self-replicating genetic element comprised of DNA or RNA that replicates from one origin of replication. In some embodiments, the replicon is a viral replicon. In some embodiments, the replicon is an alphavirus replicon. Distinct from host mRNA, alphavirus replicon RNAs encode a set of four nonstructural proteins (nsPs 1-4) that are responsible both for genome replication and, when engineered to include genes encoding non-virus products, such as "cargo" proteins, provide for transcription of such "cargo" products under the subgenomic promoter.

Alphaviruses are part of the IV Togaviridae family of viruses, possess a positive sense, single-stranded RNA genome, and are characterized by an icosahedral nucleocapsid. The alphavirus genus includes 26 enveloped viruses that infect eukaryotes. Alphaviruses have a broad host range and are transmitted by mosquitos and hematophagous arthropods. Non-limiting examples of alphaviruses include Venezuelan equine encephalitis (VEE), Eastern Equine Encephalitis (EEE), Western equine encephalitis (WEE), Everglades (EVE), Mucambo (MUC), Pixuna (PIX), Semliki Forest (SF), Middelburg (MID), Chikungunya (CHIK), O'Nyong-Nyong (ONN), Ross River (RR), Barmah Forest (BF), Getah (GET), Sagiyama (SAG), Bebaru (BEB), Mayaro (MAY), Una (UNA), Sindbis (SIN), Aura (AURA), Babanki (BAB), Highlands J (HJ), and Fort Morgan (FM).

Of the non-structural proteins, nsP1 is required for initiation of synthesis of minus-strand RNA, nsP2 has been shown to be regulate the synthesis of the 26S subgenomic RNA and regulate the cytopathic effect of alphavirus infection. The role of nsP3 role is not well understood but prior art focused on SIN alphavirus suggests that it is involved in subgenomic transcription. nsP4 has been shown to encode the RNA polymerase of the alphavirus. In one embodiment, the alphavirus replicon has non-structural proteins present, but has genes encoding its structural proteins deleted.

As used herein, the term "deleted" or "deletion" refers to total deletion of the specified segment or the deletion of a sufficient portion of the specified segment to render the segment inoperative or nonfunctional. Methods for deletion are well established in the art can be found in U.S. Pat. No. 4,650,764.

As used herein, the term "subgenome" or "subgenomic" refers to a smaller section of the whole replicon genome. Accordingly, subgenomic transcription, as used herein, refers to the transcription of one or more genes in the replicon genome but not all the genes constituting the replicon genome. In one embodiment, subgenomic transcription refers to transcription of the genes of experimental or therapeutic interest, which are described elsewhere herein.

In some embodiments, the alphavirus replicon as used herein encodes non-structural proteins for replication, but does not encode structural proteins for viral formation. In some embodiments, the alphavirus replicon is a self-replicating RNA engineered from alphaviruses. In some embodiments, the alphavirus replicon includes the untranslated regions, non-structural proteins, and subgenomic promoter of the alphavirus.

In some embodiments, the structural proteins of the replicon are replaced by one or more gene(s) of experimental or therapeutic interest. For example, the alphavirus replicons can encode therapeutic genes or antigens under control of (i.e., operably linked to) a subgenomic promoter, in place of the structural proteins required for virus replication. Thus, in some embodiments, the alphavirus replicon comprises a gene encoding a therapeutic agent, e.g., polypeptide, such as a cytokine, a chemokine, or a growth factor. In some embodiments, the therapeutic agent is an anti-tumor agent.

In some embodiments, the gene(s) of experimental or therapeutic interest encode cytokines, chemokines, or growth factors. Cytokines are known in the art, and the term itself refers to a generalized grouping of small proteins that are secreted by certain cells within the immune system and have an effect on other cells. Cytokines are known to enhance the cellular immune response and, as used herein, can include, but are not limited to, TNFα, IFN-γ, IFN-α, TGF-β, IL-1, IL-2, IL-4, IL-10, IL-13, IL-15 superagonist (IL-15Sa), IL-17, IL-18, and chemokines. Chemokines are useful for studies investigating response to infection, immune responses, inflammation, trauma, sepsis, cancer, and reproduction, among other applications. Chemokines are known in the art, and are a type of cytokines that induce chemotaxis in nearby responsive cells, typically of white blood cells, to sites of infection. Non-limiting examples of chemokines include, CCL14, CCL19, CCL20, CCL21, CCL25, CCL27, CXCL12, CXCL13, CXCL-8, CCL2, CCL3, CCL4, CCL5, CCL11, and CXCL10. Growth factors are known in the art, and the term itself is sometimes interchangeable with the term cytokines. As used herein, the term "growth factors" refers to a naturally occurring substance capable of signaling between cells and stimulating cellular growth. While cytokines may be growth factors, certain types of cytokines may also have an inhibitory effect on cell growth, thus differentiating the two terms. Non-limiting examples of growth factors include Adrenomedullin (AM), Angiopoietin (Ang), Autocrine motility factor, Bone morphogenetic proteins (BMPs), Ciliary neurotrophic factor (CNTF), Leukemia inhibitory factor (LIF), Interleukin-6 (IL-6), Macrophage colony-stimulating factor (m-CSF), Granulocyte colony-stimulating factor (G-CSF), Granulocyte macrophage colony-stimulating factor (GM-CSF), Epidermal growth factor (EGF), Ephrin A1, Ephrin A2, Ephrin A3, Ephrin A4, Ephrin A5, Ephrin B1, Ephrin B2, Ephrin B3, Erythropoietin (EPO), Fibroblast growth factor 11(FGF11), Fibroblast growth factor 2(FGF2), Fibroblast growth factor 3(FGF3), Fibroblast growth factor 4(FGF4), Fibroblast growth factor 5(FGF5), Fibroblast growth factor 6(FGF6), Fibroblast growth factor 7(FGF7), Fibroblast growth factor 8(FGF8), Fibroblast growth factor 9(FGF9), Fibroblast growth factor 10(FGF10), Fibroblast growth factor 11(FGF11), Fibroblast growth factor 12(FGF12), Fibroblast growth factor 13(FGF13), Fibroblast growth factor 14(FGF14), Fibroblast growth factor 15(FGF15), Fibroblast growth factor 16(FGF16), Fibroblast growth factor 17(FGF17), Fibroblast growth factor 18(FGF18), Fibroblast growth factor 19(FGF19), Fibroblast growth factor 20(FGF20), Fibroblast growth factor 21(FGF21), Fibroblast growth factor 22(FGF22), Fibroblast growth factor 23(FGF23), Fetal Bovine Somatotrophin (FBS), Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factor-1 (IGF-1), Insulin-like growth factor-2 (IGF-2), Interleukin-1 (IL-1), IL-2, IL-3, IL-4, IL-5, IL-6, IL-7, Keratinocyte growth factor (KGF), Migration-stimulating factor (MSF), Macrophage-stimulating protein (MSP), Myostatin (GDF-8), Neuregulin 1 (NRG1), Neuregulin 2 (NRG2), Neuregulin 3 (NRG3), Neuregulin 4 (NRG4), Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS), T-cell growth factor (TCGF), Thrombopoietin (TPO), Transforming growth factor alpha (TGF-α), Transforming growth factor beta (TGF-β), Tumor necrosis factor-alpha (TNF-α), and Vascular endothelial growth factor (VEGF). In some embodiments, the gene of experimental or therapeutic interest encodes Interleukin-2 (IL-2), a type of cytokine signaling molecule in the immune system that is known to regulate the activities of white blood cells that are responsible for immunity.

Methods of Use

The LNPs and LPRs disclosed herein may be used to deliver a RNA polynucleotide to a cell, e.g., to the interior of a cell. Accordingly, the disclosure provides methods of introducing a RNA polynucleotide into a cell, comprising contacting the cell with a LNP or LPR comprising or associated with the RNA polynucleotide, e.g., an alphavirus replicon. In particular embodiments, the method results in increased transfection efficiency of the cell as compared to the transfection efficiency achieved when the cell is contacted with the naked RNA polynucleotide, i.e., not encapsulated in or associated with the LNP or LPR. The increased transfection efficiency may be at least 10% greater, at least 20% greater, at least 50% greater, or at least 100% greater. In certain embodiments, it is between 10% and 100% greater. In certain embodiments, the RNA polynucleotide is an alphavirus replicon, including but not limited to any disclosed herein.

The lipid nanoparticles described herein, DOTAP:DSPC:cholesterol:DSPE-PEG2000 at a molar ratio of about 40:about 10:about 48:about 2, or compositions comprising such lipid nanoparticle and an alphavirus replicon can be used in methods of treatment. Similarly, the LPRs disclosed herein can be used in methods of treatment. Such methods include providing or administering to a subject in need of such treatment the lipid nanoparticle or LPR, or the compositions comprising such lipid nanoparticle or LPR and an alphavirus replicon.

Thus, according to another aspect, methods of delivering alphavirus replicons in vivo are provided. In certain embodiments, the methods comprises providing to a subject a composition comprising a LNP or LPR disclosed herein and one or more alphavirus replicon. The methods can also include preparing a mixture of an alphavirus replicon and the lipid nanoparticles or LPRs described herein, and administering the mixture into a subject. The disclosed methods can apply in an experimental, veterinary, and medical context. In some embodiments the subject is a mammal, such as a human. In some embodiments, the subject is an animal (e.g., animal model). In other embodiments the subject is a mouse. Subjects also include animals such as household pets (e.g., dogs, cats, rabbits, ferrets, etc.), livestock or farm animals (e.g., cows, pigs, sheep, chickens and other poultry), horses such as thoroughbred horses, laboratory animals (e.g., rats, rabbits, etc.), and the like.

The lipid nanoparticles (LNPs) described herein may be used to deliver pharmaceutical therapies to targeted locations. One example is a lipid nanoparticle as described herein, which includes an alphavirus replicon that encodes and expresses a therapeutic agent.

In certain embodiments, the disclosure provides methods of treating a cancer or tumor in a subject in need thereof, comprising providing to the subject a composition disclosed herein comprising a LNP (or LPR) and an alphavirus replicon comprising a sequence encoding an anti-tumor agent operatively linked to a promoter, such that the anti-tumor agent is expressed in a cell following delivery to the subject. In particular embodiments, the anti-tumor agent causes direct tumor killing, tumor microenvironment remodeling, and/or triggering of an anti-tumor immune response. In particular embodiments, the composition is provided to the subject systemically or intratumorally, and in some embodiments, the tumor is a solid tumor.

The lipid nanoparticles, LPRs, and compositions described herein can be administered in a variety of manners, e.g., as an injection, using different delivery routes. In particular embodiments, they are administered parenterally or orally. In certain embodiments, the lipid nanoparticles, LPRs, and compositions of the present disclosure can be administered intravenously, intradermally, intraarterially, intralesionally, intratumorally, intracranially, intraarticularly, intraprostatically, intrapleurally, intratracheally, intranasally, intravitreally, intravaginally, intrarectally, topically, intramuscularly, intraperitoneally, subcutaneously, subconjunctivally, intravesicularly, mucosally, intrapericardially, intraumbilically, intraocularally, orally, locally, inhalation (e.g., aerosol inhalation), injection, infusion, continuous infusion, localized perfusion bathing target cells directly, via a catheter, via a lavage, in creams, or by other method or any combination of the forgoing as would be known to one of ordinary skill in the art (see, for example, Remington's Pharmaceutical Sciences (1990), incorporated herein by reference). In a particular embodiment, intraperitoneal injection is contemplated. In a particular embodiment, intratumoral injection is contemplated.

In some embodiments, the LNPs or LPRs with alphavirus replicons can be used in the treatment of cancer. In certain embodiments, the cancer is a solid tumor or a liquid tumor. In particular embodiments, the cancer can be a carcinoma, e.g., a sarcoma or a melanoma. Carcinomas include, but are not limited to, basal cell carcinoma, biliary tract cancer, bladder cancer, breast cancer, cervical cancer, choriocarcinoma, central nervous system cancer, colon and rectum cancer, kidney or renal cell cancer, larynx cancer, liver cancer, small cell lung cancer, non-small cell lung cancer (NSCLC, including adenocarcinoma, giant (or oat) cell carcinoma, and squamous cell carcinoma), oral cavity cancer, ovarian cancer, pancreatic cancer, prostate cancer, skin cancer (e.g., basal cell cancer, melanoma, or squamous cell cancer), stomach cancer, testicular cancer, thyroid cancer, uterine cancer, rectal cancer, cancer of the respiratory system, and cancer of the urinary system. In certain embodiments, the methods disclosed herein comprise treating a tumor in a subject in need thereof, comprising providing a composition disclosed herein that encodes an anti-tumor agent to the subject by intratumoral injection. In particular embodiments, the tumor is a skin cancer, a breast cancer, a head and neck cancer, or a lymphoma.

In some embodiments, the LNPs or LPRs with alphavirus replicons can be used in animal models of cancer. In one embodiment, the animal model is a mouse model of B16F10 melanoma. B16F10 melanoma is a murine tumor cell line that is used as a model for human skin cancers, and is a useful model for researching therapeutic interventions relating to metastasis and solid tumor formation. In some embodiments, the lipid nanoparticles are injected intratumorally. Intratumorally is a term known in the art, and refers to an injection being placed within a tumor. In some embodiments, the lipid nanoparticles are injected intramuscularly. Intramuscularly is a term known in the art, and refers to an injection being placed within a muscle.

In some embodiments, the lipid nanoparticles or LPRs are administered by injection in the form of a pharmaceutical composition (e.g., LNP composition or LPR composition). Pharmaceutical compositions may be sterile compositions that include the lipid nanoparticles or LPRs described herein (e.g., in combination with an alphavirus replicon), preferably in a pharmaceutically-acceptable carrier. This term requires that the pharmaceutical composition be nontoxic and sufficiently pure so that no further manipulation of the composition is needed prior to administration to the subject. The term "carrier" denotes an organic or inorganic ingredient, natural or synthetic, with which the cells, nanoparticles and agent(s) are combined to facilitate administration. The components of the pharmaceutical compositions are combined in a manner that precludes interaction that would substantially impair their desired pharmaceutical efficiency. Moreover, for animal (e.g., human) administration, it will be understood that preparations should meet sterility, pyrogenicity, general safety and purity standards as required by FDA Office of Biological Standards. The compounds are generally suitable for administration to humans or mammals. Compositions for lipid nanoparticles with biological active molecules and suitable carriers are disclosed in U.S. Pat. No. 7,404,969.

The lipid nanoparticles, LPRs, LNP composition, or LPR composition can be administered once, or alternatively they may be administered in a plurality of administrations. If administered multiple times, the lipid nanoparticles, LPRs, the LNP composition, or LPR composition may be administered via different routes. For example, the first (or the first few) administrations may be made directly into the affected tissue or tumor while later administrations may be systemic.

As used herein, the term "pharmaceutically-acceptable carrier" refers to one or more compatible solid or liquid filler, diluents or encapsulating substances which are suitable for administration to a human or other subject contemplated by the disclosure. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers (e.g., antioxidants), gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The following examples are provided to illustrate specific instances of the practice of the present disclosure and are not intended to limit the scope of the invention. As will be apparent to one of ordinary skill in the art, the present invention will find application in a variety of compositions and methods.

EXAMPLES

Example 1: LNP Synthesis

An ethanol dilution method was used to produce the LNP formulation. DOTAP, DSPC, Cholesterol and DSPE-PEG 2000 were mixed in ethanol with the molar ratios of 40:10:48:2. RNA was dissolved in citrate buffer (pH 6) with 8:1 N:P molar ratio calculated based on the mole of DOTAP. The volume of the citrate buffer was identical to the volume of ethanol. The citrate buffer with RNA was added into the ethanol with lipids, and another equal volume of citrate buffer was immediately added. The bulk solution was quickly mixed for about 30 s. The mixture was equilibrated for 1 h at room temperature with gentle shake. Next, the LNP was dialyzed against PBS for at least 1 h. The resulting LNP was collected and stored at 4° C. before use.

Example 2: LPR Synthesis

LPR core was prepared by mixing 4 μg RNA replicon and 3 μg protamine in RNase-free water. The RNA and protamine mixture was placed at room temperature for 10 mm. Then, 19.6 μL 20 mM DOTAP/cholesterol (1:1, mol:mol) liposomes was mixed with the RNA/protamine solution, and incubated at room temperature for 10 min. PEGylation was performed by adding 11.22 μg DSPE-PEG, and incubating the mixture at 50° C. for 10 mM. The resulting LPR was cooled to room temperature and stored at 4° C. before use.

Example 3: Alphavirus Replicons

The Alphaviral replicon DNA template for in vitro transcription (IVT) was generated by Gibson assembly using synthetic DNA fragments based on the sequence of the Venezuelan equine encephalitis (VEE) TC-83 strain containing a A3G mutation in the 5'UTR. VEE replicon RNA was produced by run-off IVT of I-SceI-digested replicon plasmid DNA using the MEGAscript® T7 Transcription Kit, followed by purification using the RNeasy® Mini Kit (Qiagen), denaturation of the RNA at 65 degrees C., enzymatic (cap1) capping of the RNA using the ScriptCap™ 2'-O-Methyltransferase Kit (Cellscript) and ScriptCap™ m7G Capping System (Cellscript), and a final purification using the RNeasy® Mini Kit (Qiagen) following the manufacturers' protocols.

Example 4: Intratumoral Delivery of Replicons by LNPs

Figure 10:
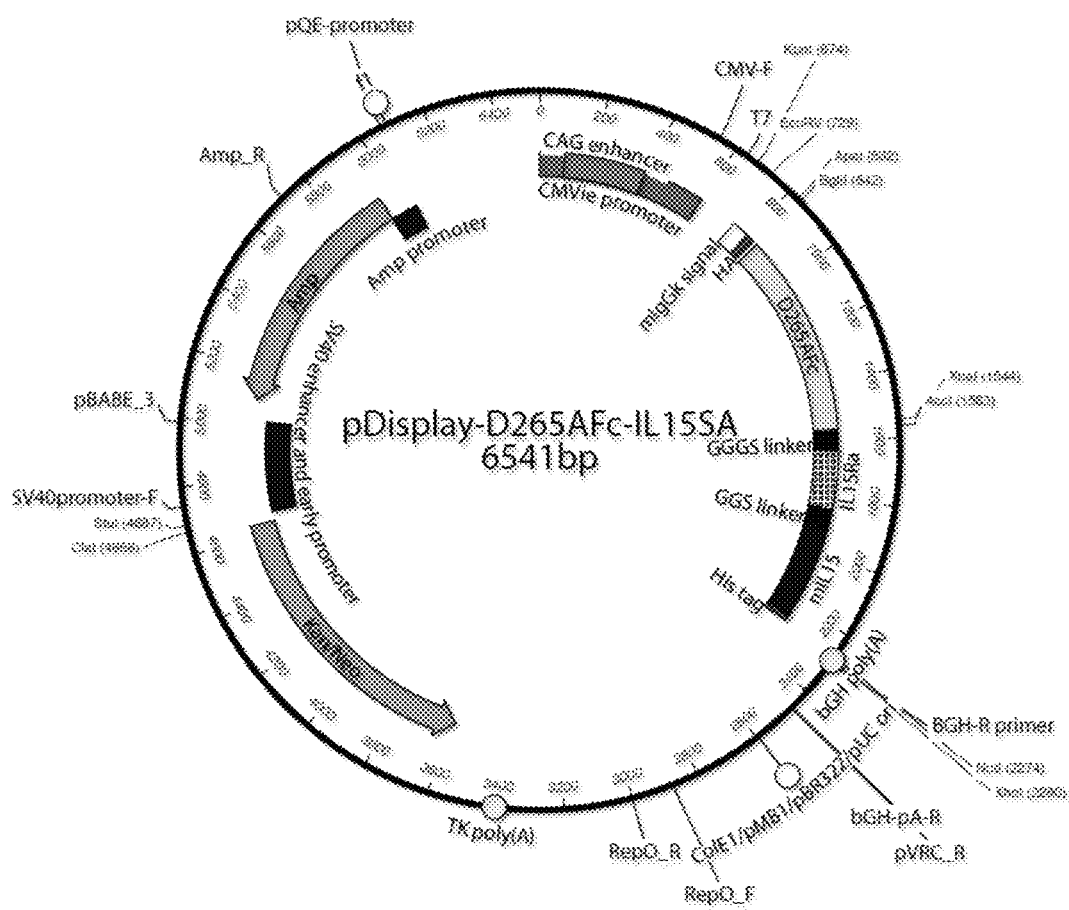
FIG. 10. A diagram of an illustrative IL-15Sa replicon construct that includes the payload present in the construct used in the experiments.

Replicons encoding IL-15 superagonist (IL-15Sa, a fusion of IL-15, the IL-15 receptor a chain, and an Fc protein) were formulated in the above-described LNPs as a candidate immunomodulatory drug to be expressed within tumors and drive anti-tumor immune responses. The IL-15Sa comprised the following sequences in the following order from N-terminus to C-terminus:(Murine IgGk secretion signal)-(HA tag)-(Fc variant)-(murine IL15 Receptor alpha "sushi domain")-(GS linker)-(murine IL15)-(His tag). The IL-15Sa was based on the IL-15Sa described in Stone, J. D. et al., Biotechnol. Frog., 2012, Vol. 28, No. 6 (DOI 10.1002/btpr.1631; published online Oct. 18, 2012 in Wiley Online Library (wileyonlinelibrary.com).). A map of a related construct containing the same payload is shown in FIG. 10.

Figure 1B:
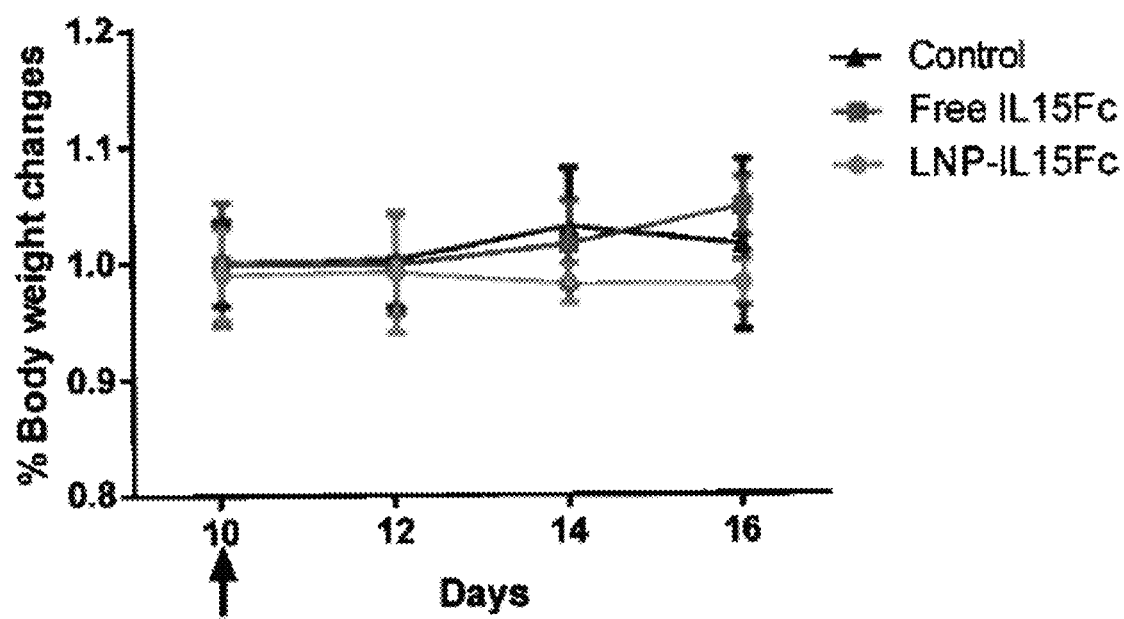
Figure 1C:
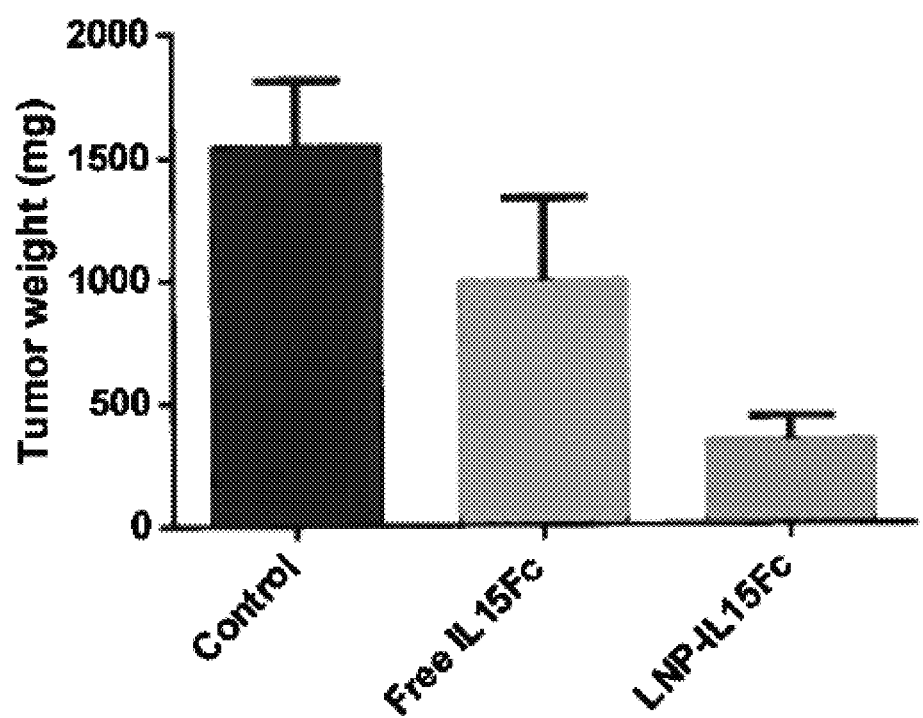
Figure 1D:
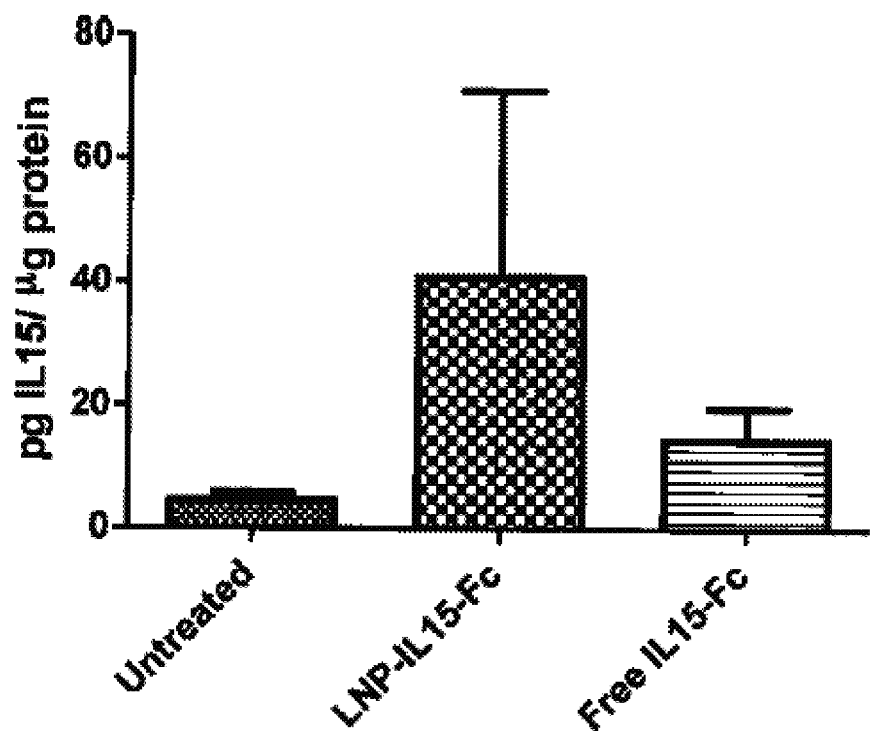
Figure 1E:
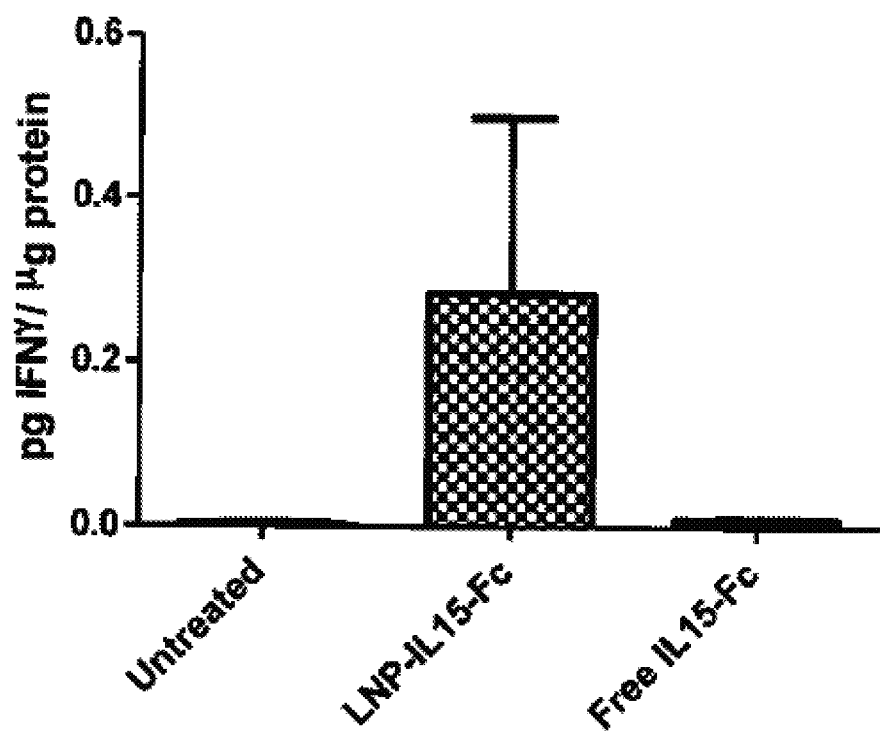

As shown in FIG. 1A, a single intratumoral injection of LNPs carrying IL-15Sa replicon on day 10 slowed B16F10 tumor growth compared to injection of an equivalent dose of "free" replicons not encapsulated in LNPs. Replicons were non-toxic as read out by lack of body weight changes in treated animals (FIG. 1B), though tumor mass following treatment was substantially reduced (FIG. 1C). LNP delivery of IL-15Sa replicon led to readily detectable IL-15Sa protein in the tumors, as well as IFN-γ, a signature of activated lymphocyte responses against the tumor (FIG. 1D, E).

Figure 2A:
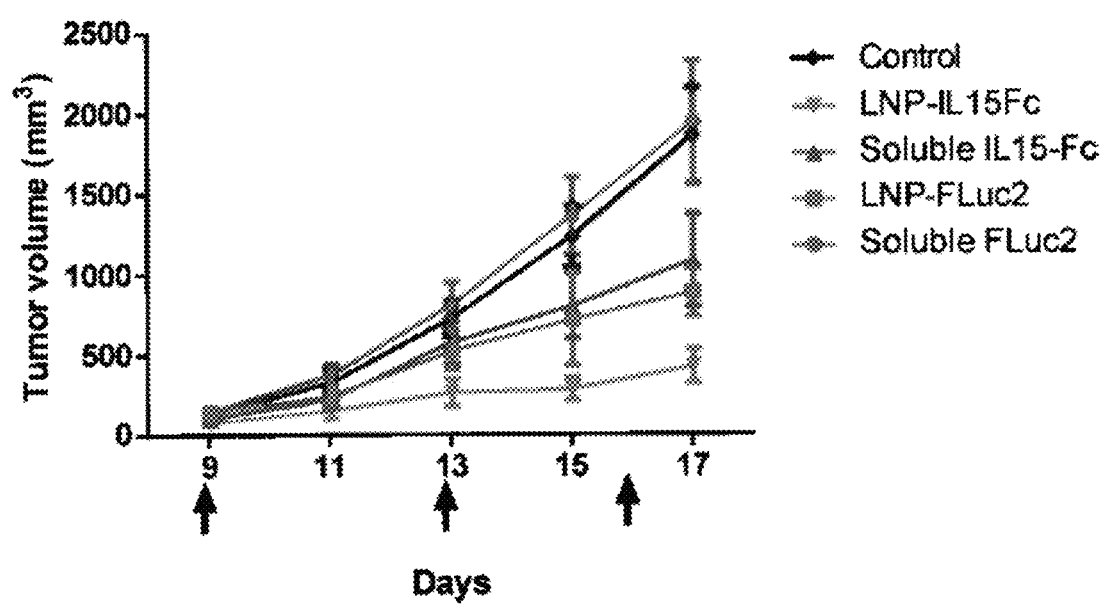
FIGS. 2A-2C. C57BL/6 mice were inoculated with 0.5M B16F10 cells subcutaneously in the right flank and given intratumoral injections on day 9, 13, 16, with 5 µg/dose.
Figure 2B:
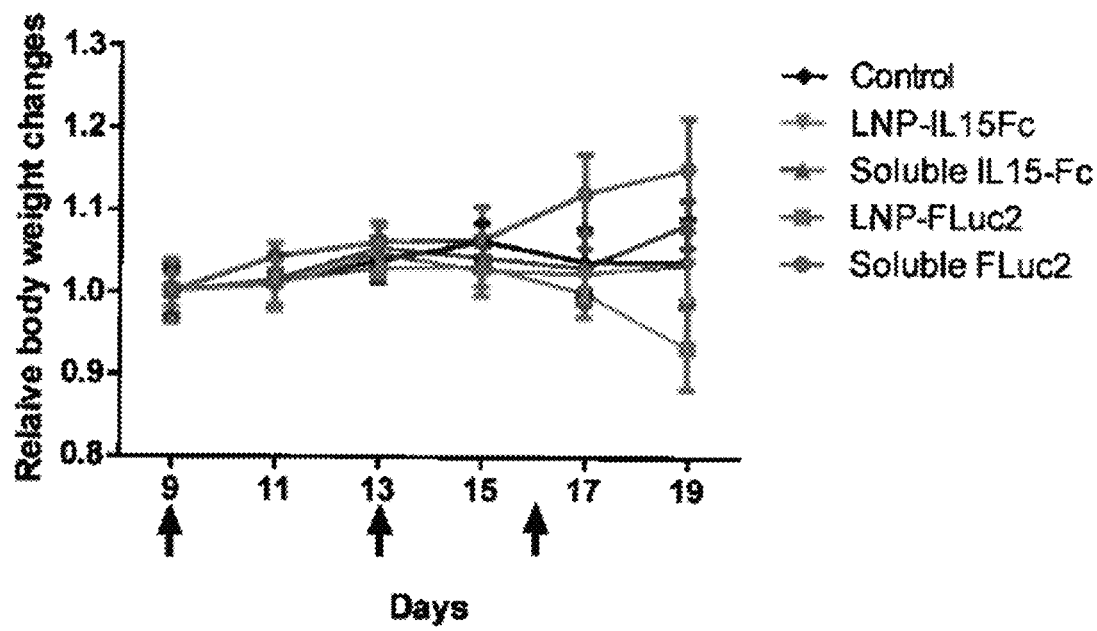
Figure 2C:
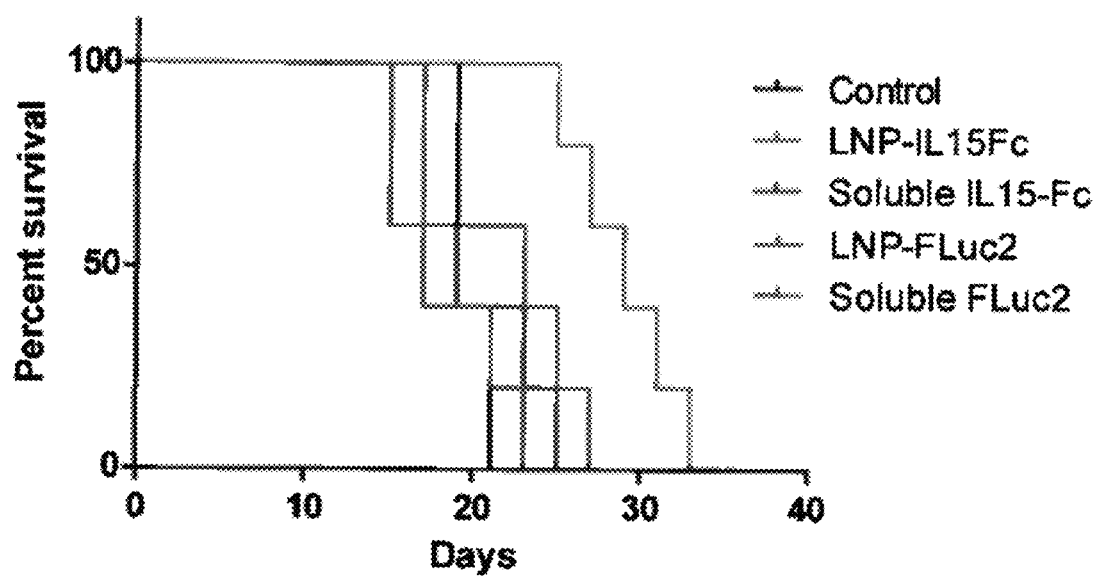
Figure 3:
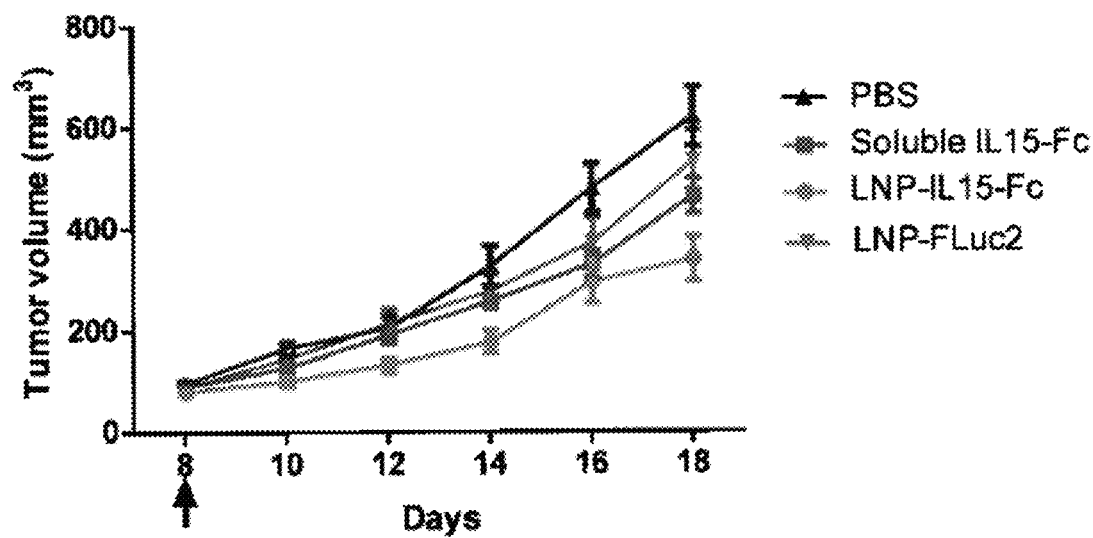
FIG. 3. BALB/c mice were inoculated with 4T1-TdTomato-FLuc2 cells orthotopically in the nipple and given intratumoral injections on day 8, with 5 µg/dose. Tumor growth inhibition.
Figure 4A:
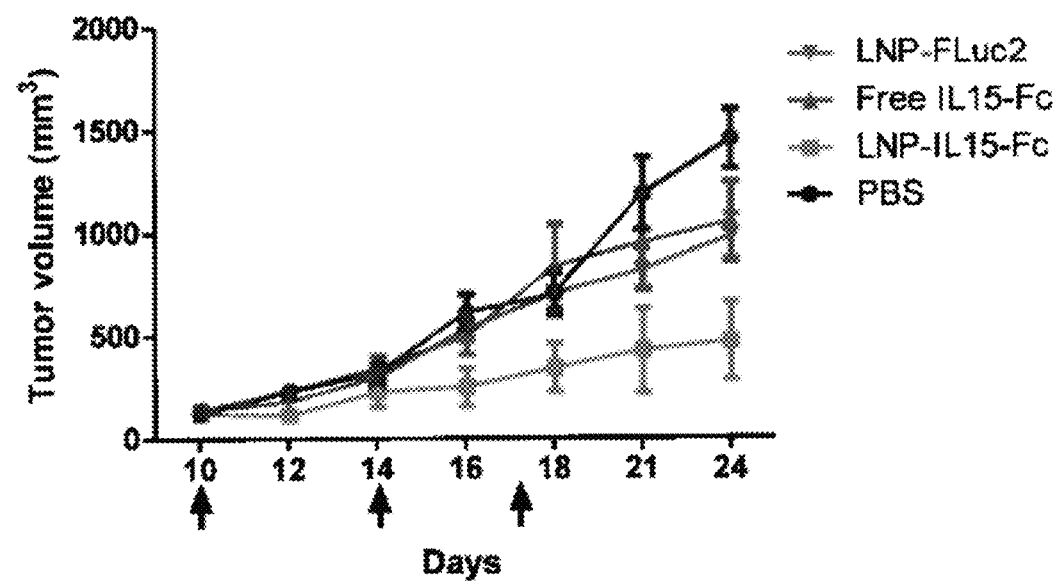
FIGS. 4A-4C. BALB/c mice were inoculated with 4T1-TdTomato-FLuc2 cells orthotopically in the nipple and given intratumoral injections on day 10, 14, 17, with 5 µg/dose.
Figure 4B:
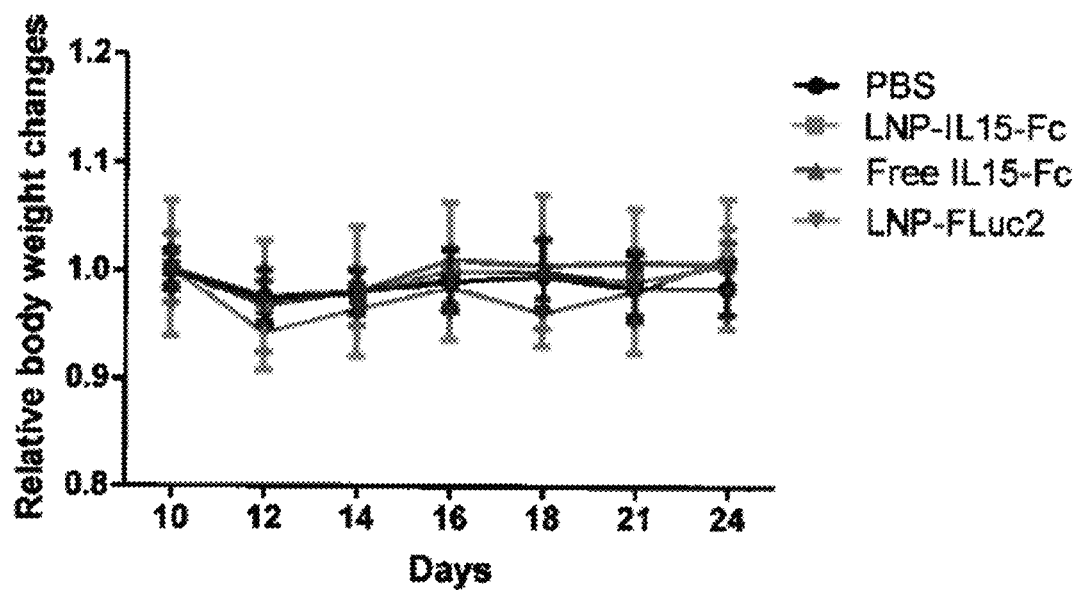
Figure 4C:
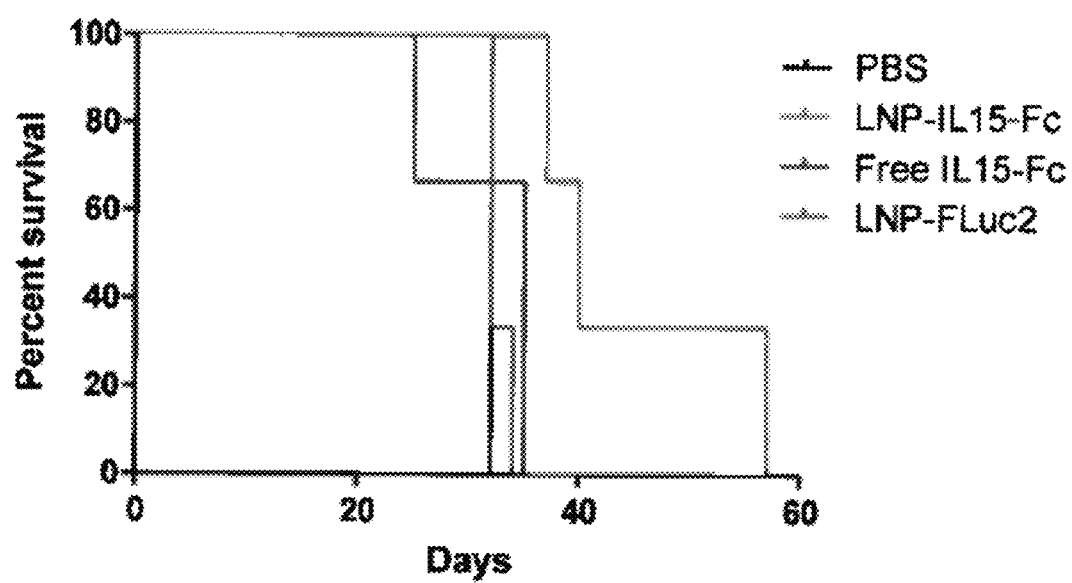

Next, LNP delivery of IL-15Sa vs. control replicons encoding luciferase (luc replicon) as a nonfunctional protein cargo was compared, and the efficacy of repeated replicon injection was tested. As shown in FIG. 2A, injection of free luc replicon led to no difference in tumor growth vs. untreated, suggesting lack of significant innate immune response induction by the naked replicon, although free IL-15Sa replicon did elicit some weak anti-tumor activity, suggesting some level of IL-15Sa production for free replicon injection. However, this response was inferior to the anti-tumor activity of LNP-IL-15Sa delivery. Repeated replicon injection showed minor toxicity with only modest weight loss following 3 injections for all formulations (FIG. 2B). As expected from the tumor size data. LNP-IL-15Sa provided the greatest survival advantage among the different replicon formulations (FIG. 2C). LNP-IL-15Sa also had anti-tumor activity in the setting of orthotopic 4T1 tumors, although with less efficacy following a single injection (FIG. 3). When administered repeatedly, however, LNP-IL-15Sa was also effective in this breast tumor model (FIG. 4).

Figure 5A:
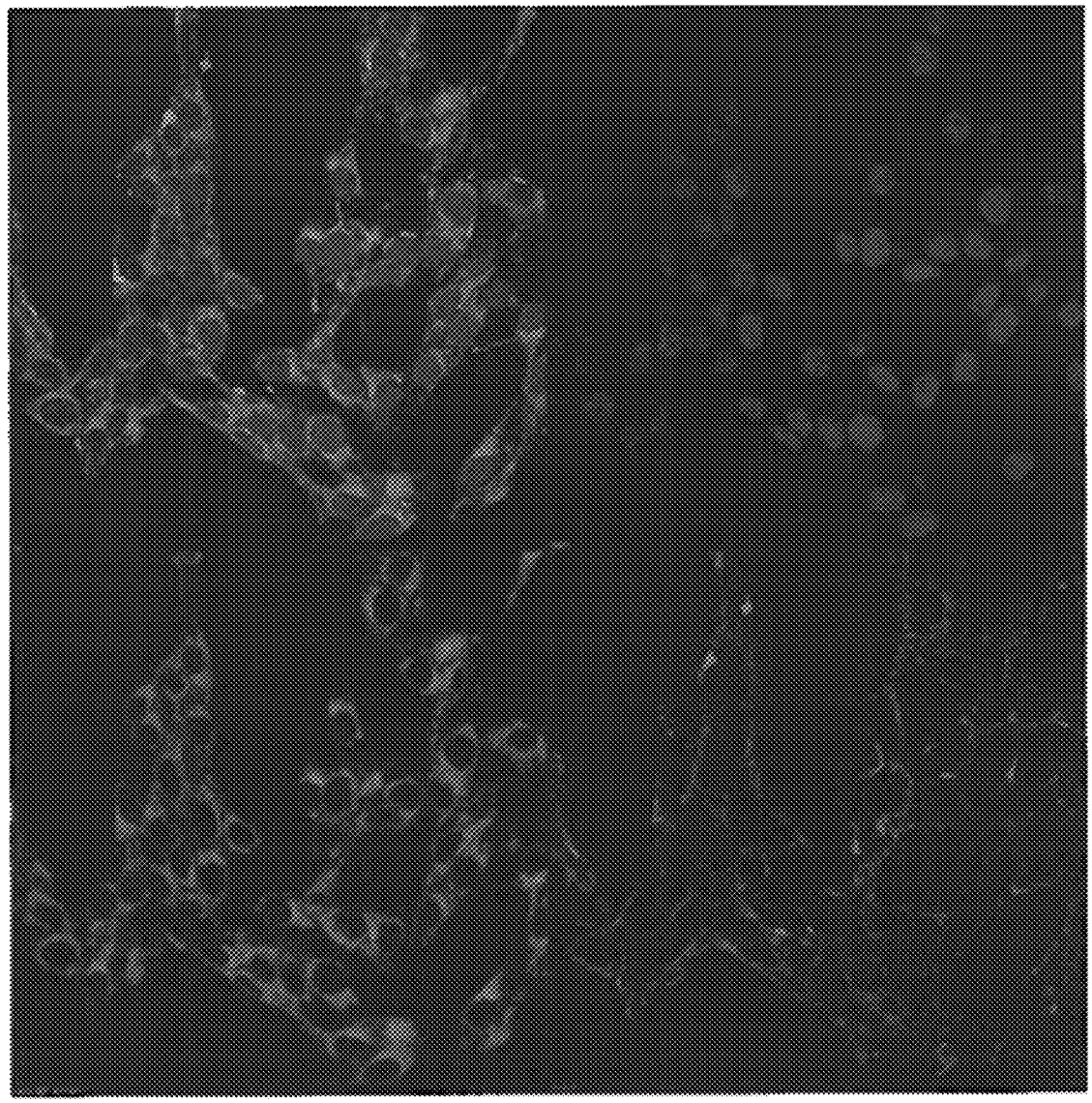
FIG. 5A-5B. B16F10 (FIG. 5A) and 4T1 (FIG. 5B) cells were incubated with fluorescence labeled LNP for 3 h. Cellular uptake was visualized by confocal microscopy. Nuclei—blue DAPI (upper right). Lipid—green NBD (lower left). Replicon—red Cy3 (lower right). Overlay (upper left).
Figure 5B:
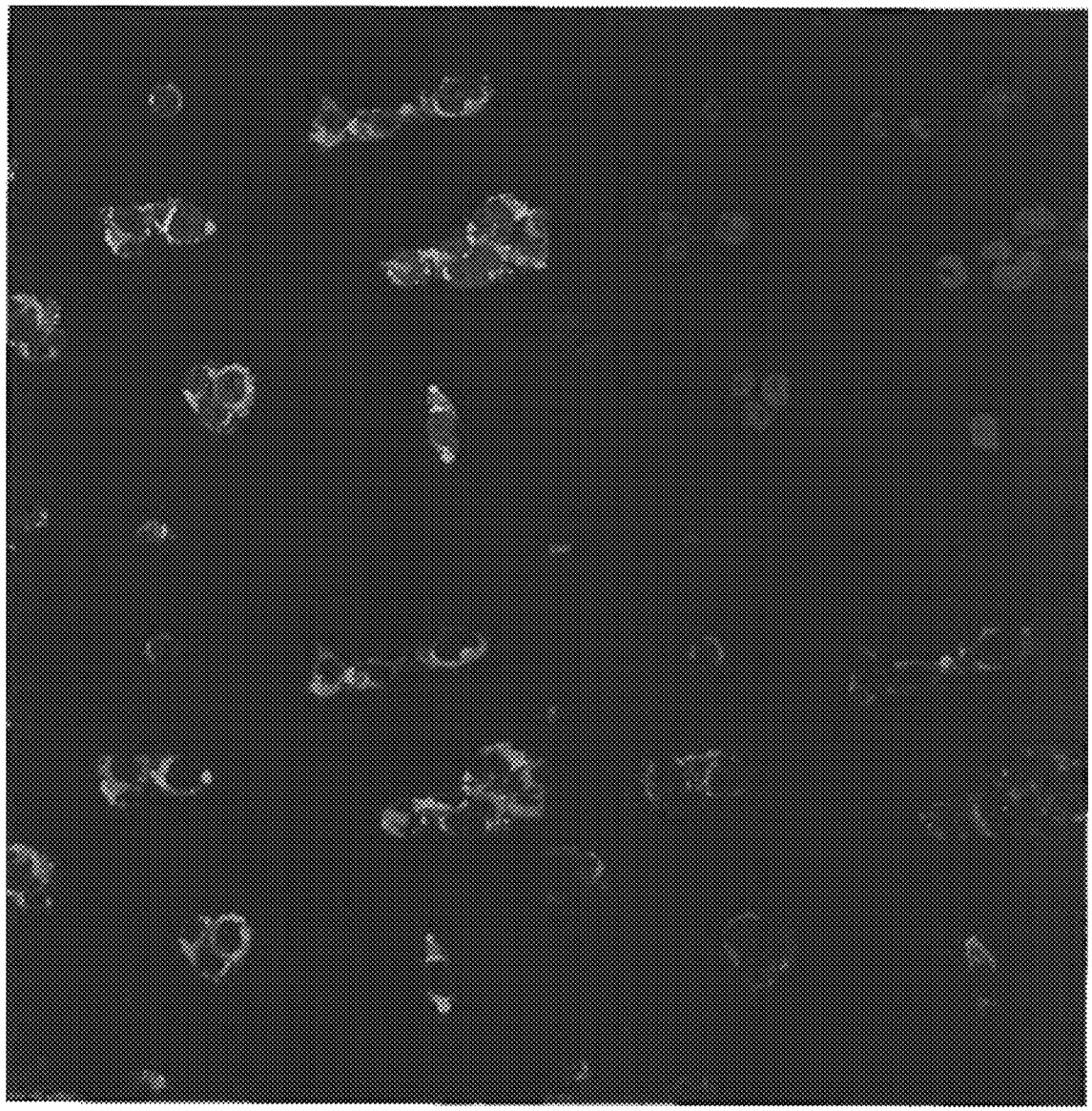
Figure 6A:
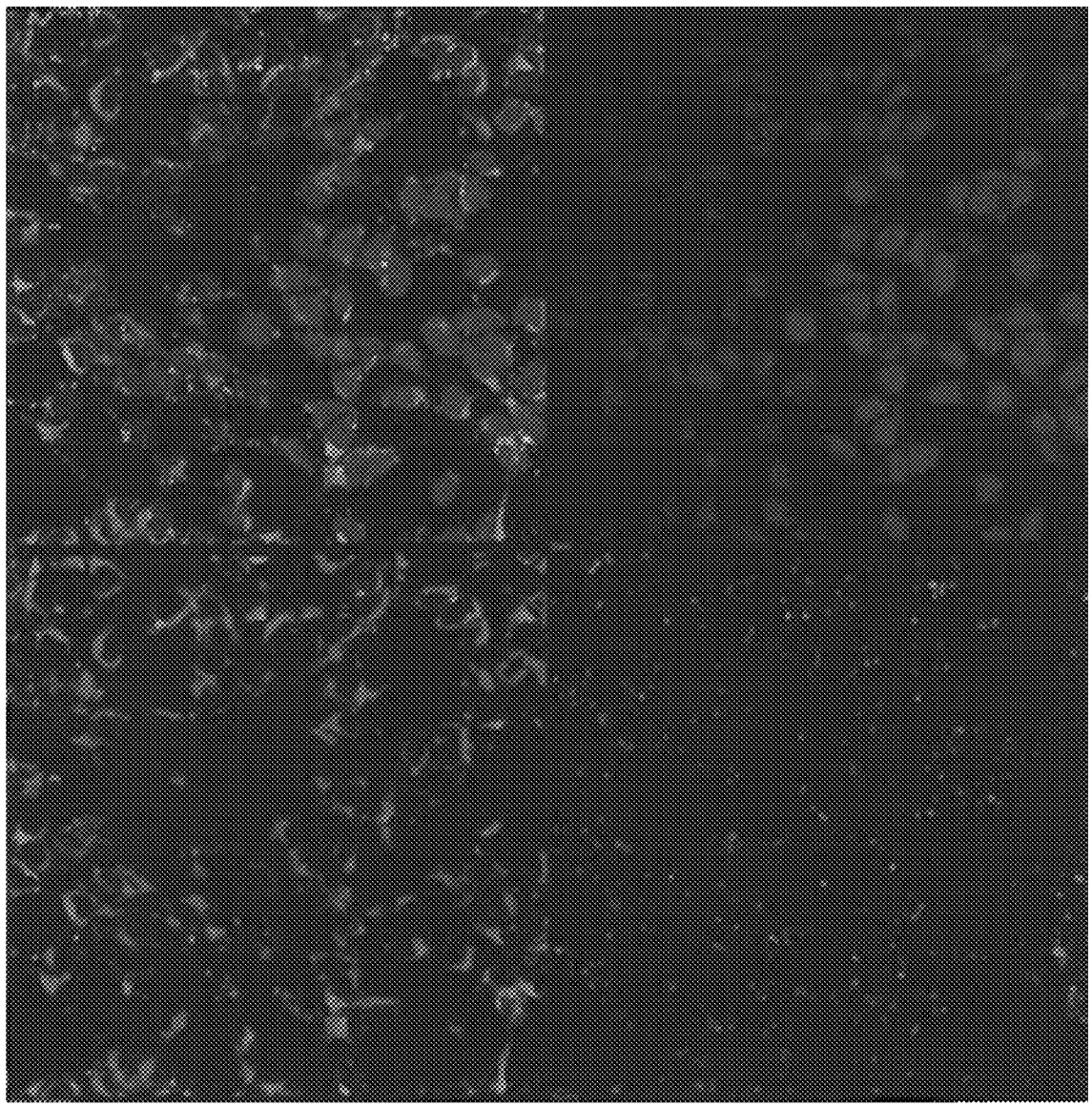
FIGS. 6A-6B. B16F10 (FIG. 6A) and 4T1 (FIG. 6B) cells were incubated with fluorescence labeled LPR for 3 h. Cellular uptake were visualized by confocal microscopy. Nuclei—blue DAPI (upper right). Lipid—green NBD (lower left). Replicon—red Cy3 (lower right). Overlay (upper left).
Figure 6B:
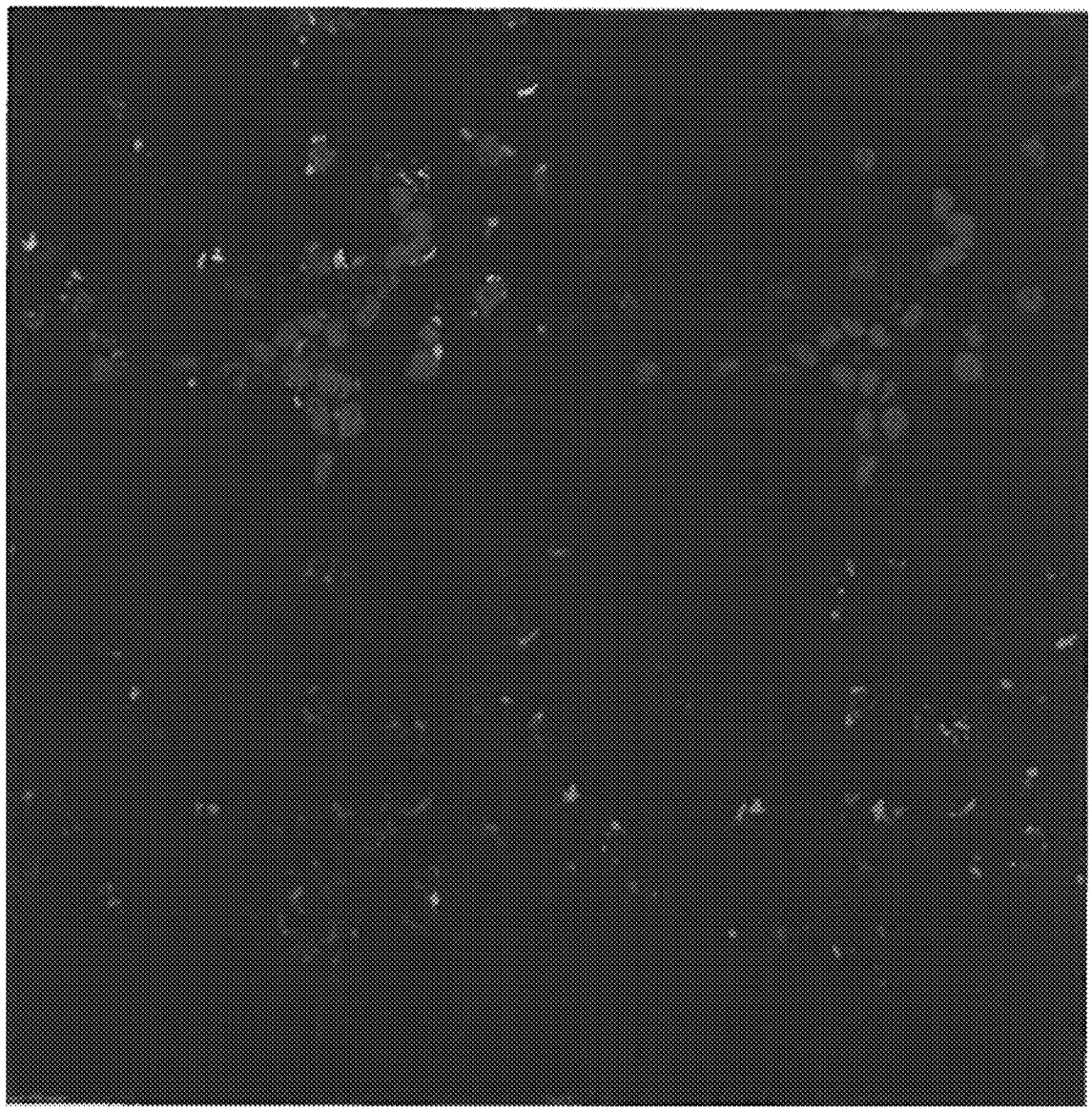
Figure 7A:
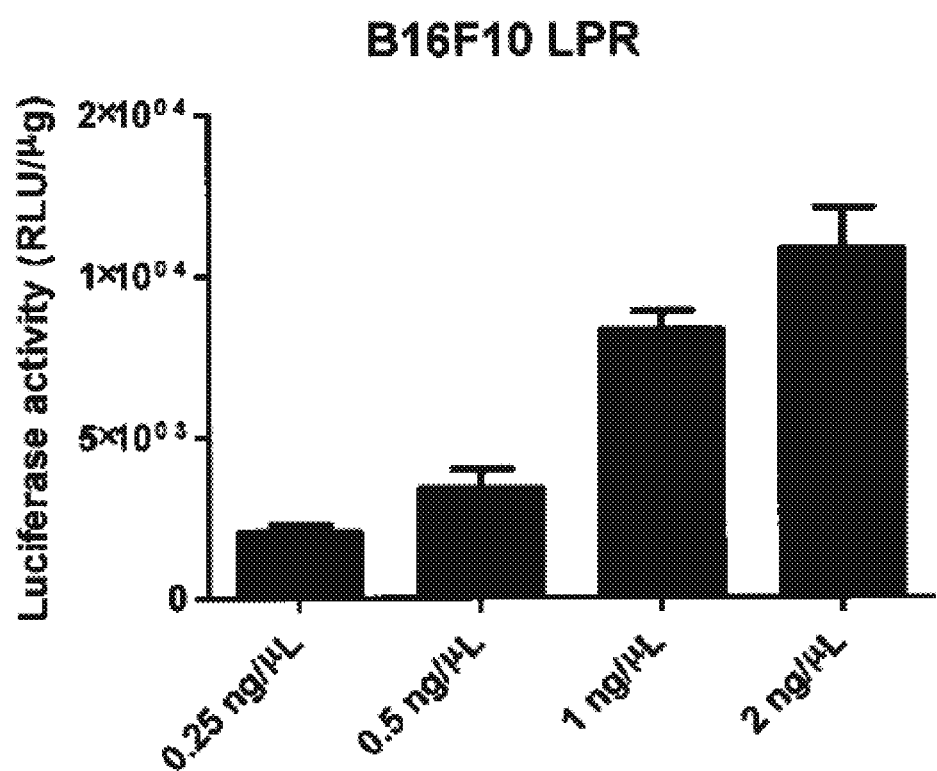
FIG. 7A-7B. B16F10 (FIG. 7A) and 4T1 (FIG. 7B) were transfected with LPR encapsulating RNA replicon encoding FLuc2 for 24 hr. The transfection efficiencies were determined by luciferase assay normalized by protein amount.
Figure 7B:
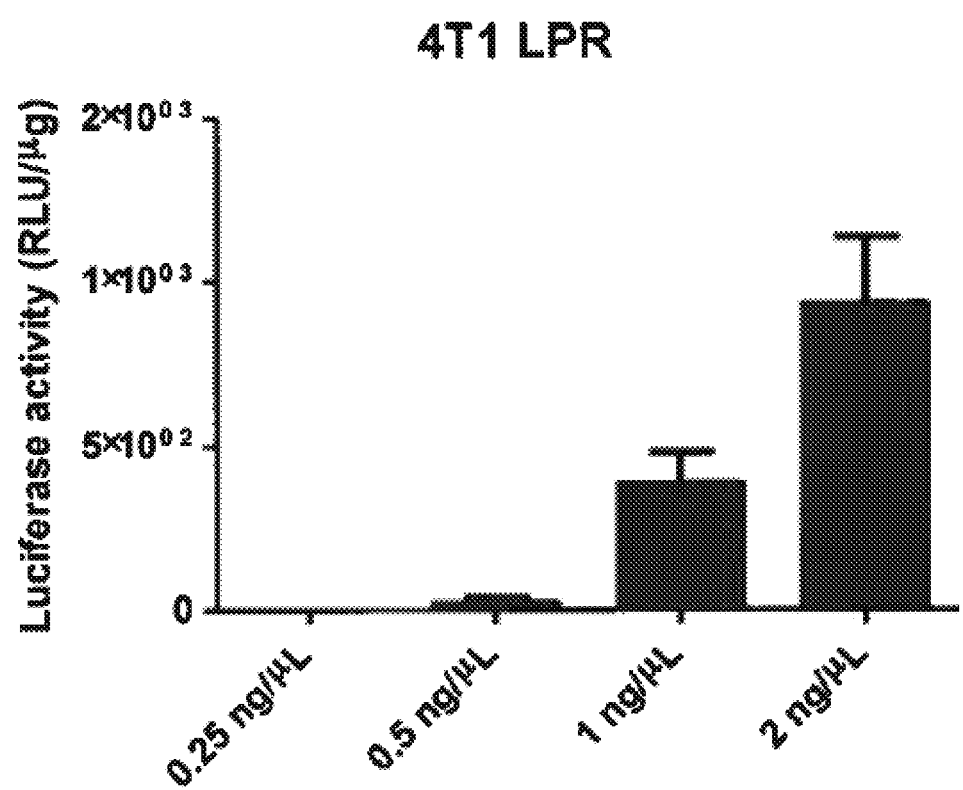

In vitro analysis of LNP and LPR uptake by B16F10 and 4T1 tumor cells in vitro revealed that the LNP formulation promoted strong association of lipids and replicon RNA with tumor cells and uptake into both cell types (FIG. 5 and FIG. 6). LPR transfected B16F10 and 4T1 cells in a dose-dependent manner, and the transfection efficiency in B16F10 cells was higher than 4T1 cells (FIG. 7).

Figure 8:
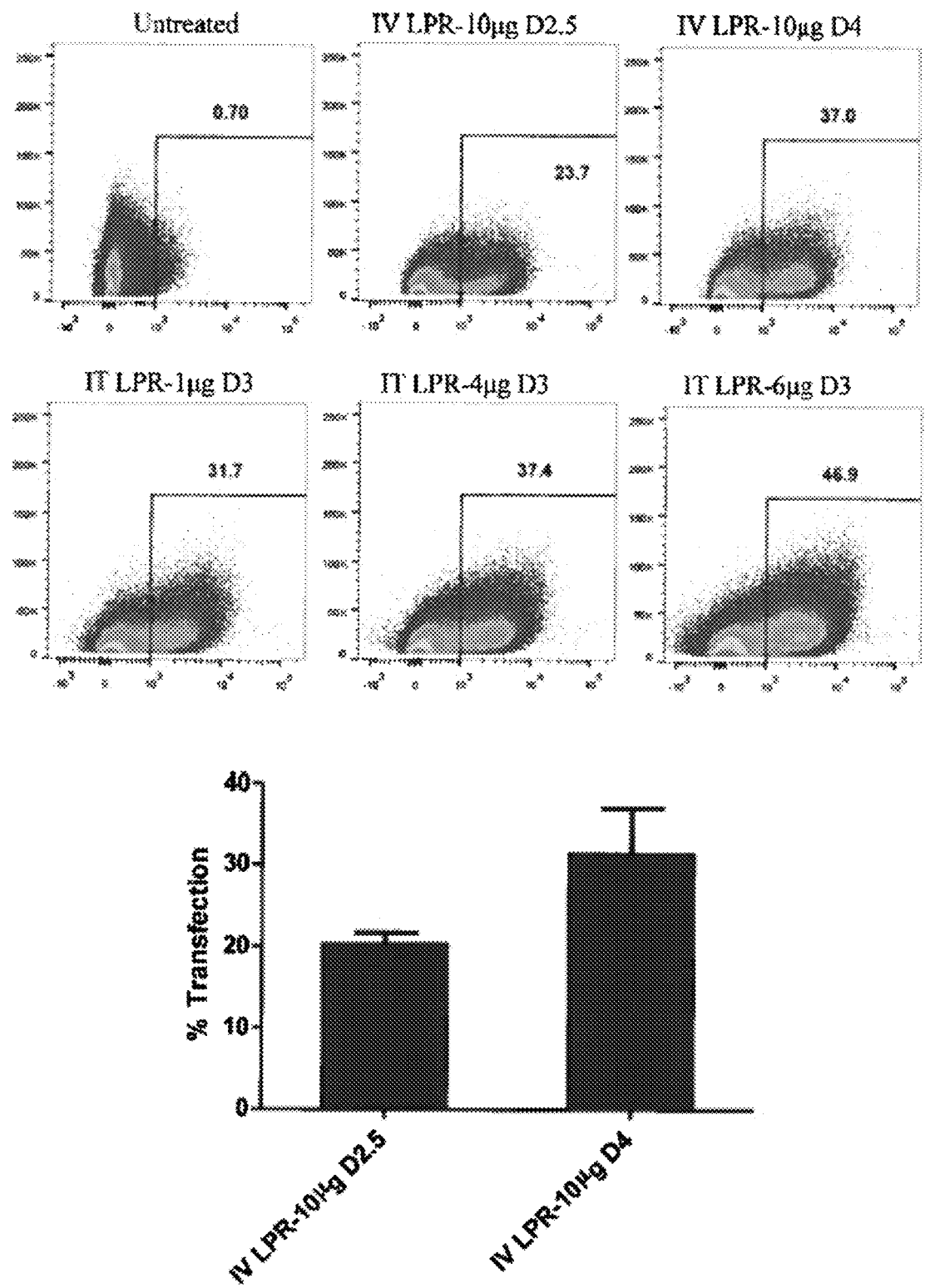
FIG. 8. C57BL/6 mice were inoculated with 0.5M B16F10 tumor cells subcutaneously. The tumor bearing mice were given intravenous (IV) or intratumoral (IT) injection of RNA replicon encoding FLuc2. During day 2.5 (D2.5)~day 4 (D4), tumors were processed to single cell suspension. Luciferase expression in tumors were detected by intracellular staining with anti-luciferase antibody Tumor cells were gated on live cells and CD45− cell population.

LPR was able to transfect B16F10 tumors via both intratumoral (IT) and intravenous (IV) administration routes (FIG. 8). Besides suppressing the growth of solid tumors by local injection, LPR can also be administered systemically to retard the growth of metastasis tumor nodules or tumors that develop in deep-seated organs.

Figure 9A:
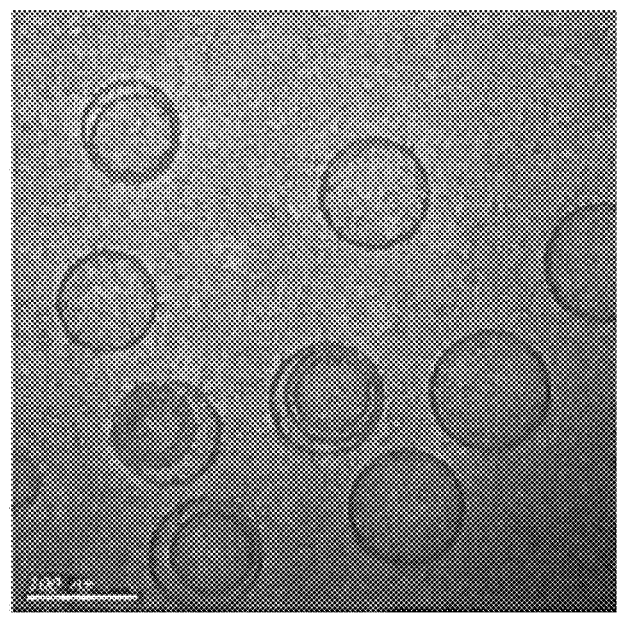
FIG. 9A-9B. Cryo-TEM images of (FIG. 9A) LNP and (FIG. 9B) LPR nanoparticles encapsulating RNA replicon.
Figure 9B:
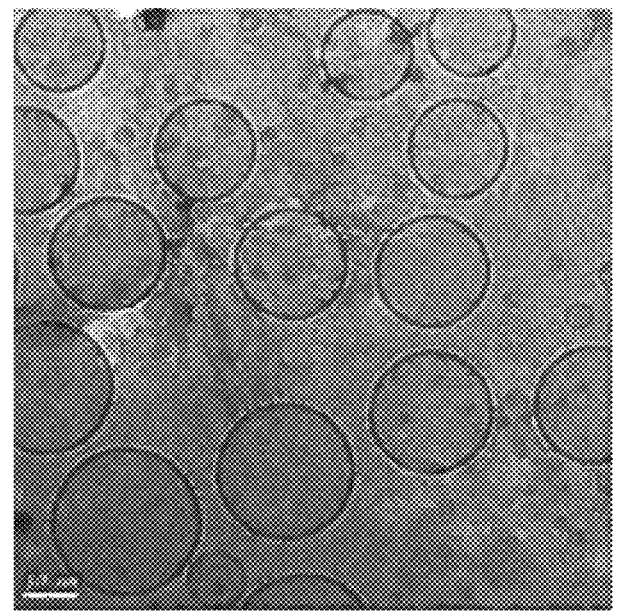

LNP and LPR were spherical in shape and had particle sizes around 100 nm (FIG. 9). The surface charge for LNP was close to neutral, and LPR had a surface charge around 25 mV (data not shown).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

Equivalents and Scope

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A lipid nanoparticle comprising 1,2-dioleoyl-3-trimethylammonium propane (DOTAP), 1,2-distearoyl-sn-glycero-3-phosphocholine (DSPC), cholesterol, and 1,2-distearoyl-sn-glycero-3-phosphoethanolamine-N-[amino(polyethylene glycol)-2000] (DSPE-PEG2000), wherein the molar ratio of DOTAP: DSPC: cholesterol: DSPE-PEG2000 is 40:10:48:2.

2. The lipid nanoparticle of claim 1, consisting of DOTAP: DSPC:
   cholesterol:DSPE-PEG2000 at a molar ratio of 40:10:48:2.

3. The lipid nanoparticle of claim 1, wherein the lipid nanoparticle is about 100 nM in diameter.

4. The lipid nanoparticle of claim 1, wherein the surface charge of the lipid nanoparticle is about neutral to about 25 mV.

5. A composition comprising the lipid nanoparticle of claim 1 and one or more RNA polynucleotide.

6. The composition of claim 5, wherein the one or more RNA polynucleotide comprises one or more self-replicating RNA derived from an alphavirus.

7. The composition of claim 6, wherein the alphavirus is a Venezuelan equine encephalitis virus, optionally wherein the Venezuelan equine encephalitis virus is TC-83 or a variant thereof.

8. The composition of claim 6, wherein at least one of the self-replicating RNA comprises a 5' cap.

9. The composition of claim 6, wherein the ratio of cationic amines in the lipid nanoparticle to anionic phosphates in the self-replicating RNA (N:P ratio) is about 0.5:1 to about 20:1.

10. The composition of claim 6, wherein at least one of the self-replicating RNA comprises a sequence encoding a therapeutic agent.

11. The composition of claim 10, wherein the therapeutic agent is (i) a cytokine, a chemokine, or a growth factor, or (ii) an anti-tumor agent, optionally wherein the anti-tumor agent is interleukin-15 (IL-15) or an IL-15 superagonist.

12. The composition of claim 6, wherein the composition comprises two or more self-replicating RNAs.

13. The composition of claim 6, wherein the self-replicating RNA is present within the lipid nanoparticle.

14. A method of treating a disease or disorder in a subject in need thereof, comprising providing to the subject the composition of claim 10, wherein the self-replicating RNA comprises the sequence encoding the therapeutic agent.

15. The method of claim 14, wherein the disease or disorder is a cancer, and the therapeutic agent is an anti-tumor agent, optionally wherein the anti-tumor agent is interleukin-15 (IL-15) or an IL-15 superagonist.

16. The method of claim 15, wherein the cancer is a a breast cancer, a head and neck cancer, a lymphoma or a skin cancer, optionally wherein the skin cancer is a melanoma.

17. The method of claim 14, wherein the composition is provided to the subject systemically locally, or parenterally.

18. The method of claim 14, wherein the composition is provided in one or more doses, optionally wherein the one or more doses are two or more doses provided within two weeks of each other.

19. The method of claim 14, wherein the composition is provided at about 1 μg/dose to about 1000 μg/dose.

20. The method of claim 15, wherein the treatment inhibits tumor growth by at least 10% as compared to growth of an untreated tumor.

21. The method of claim 17, wherein the composition is provided to the subject intratumorally or intravenously.

\* \* \* \* \*

UNITED STATES PATENT AND TRADEMARK OFFICE
CERTIFICATE OF CORRECTION

PATENT NO. : 11,026,894 B2
APPLICATION NO. : 16/739197
DATED : June 8, 2021
INVENTOR(S) : Darrell J. Irvine et al.

It is certified that error appears in the above-identified patent and that said Letters Patent is hereby corrected as shown below:

In the Claims

Claim 16, Column 15, Lines 9-10:
"…wherein the cancer is a a breast cancer…"

Should read:
"…wherein the cancer is a breast cancer…"

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*